United States Patent
Moini et al.

(10) Patent No.: US 11,830,586 B2
(45) Date of Patent: Nov. 28, 2023

(54) ENHANCEMENT OF PATIENT OUTCOME FORECASTING

(71) Applicant: Kyndryl, Inc., New York, NY (US)

(72) Inventors: Mohammed Abdul Qadeer Moini, Hyderabad (IN); Erik Rueger, Ockenheim (DE); Sreenivasulu Maheshwaram, Hyderabad (IN); Gaurav Sangamnerkar, Hyderabad (IN)

(73) Assignee: KYNDRYL, INC., New York, NY (US)

( * ) Notice: Subject to any disclaimer, the term of this patent is extended or adjusted under 35 U.S.C. 154(b) by 189 days.

(21) Appl. No.: 17/115,029

(22) Filed: Dec. 8, 2020

(65) Prior Publication Data
US 2022/0181036 A1    Jun. 9, 2022

(51) Int. Cl.
G16H 50/70    (2018.01)
G16H 10/60    (2018.01)
G16H 20/10    (2018.01)
G06N 3/08     (2023.01)
G16H 15/00    (2018.01)
G16H 70/40    (2018.01)
G16H 50/20    (2018.01)

(52) U.S. Cl.
CPC .............. G16H 50/70 (2018.01); G06N 3/08 (2013.01); G16H 10/60 (2018.01); G16H 15/00 (2018.01); G16H 20/10 (2018.01); G16H 50/20 (2018.01); G16H 70/40 (2018.01)

(58) Field of Classification Search
CPC .................. G16H 20/10; G06N 3/08
See application file for complete search history.

(56) References Cited

U.S. PATENT DOCUMENTS

| | | | |
|---|---|---|---|
| 6,658,396 B1 * | 12/2003 | Tang | G16H 20/10 706/17 |
| 10,262,112 B2 | 4/2019 | Ryan | |
| 10,339,937 B2 | 7/2019 | Koll et al. | |
| 10,586,617 B1 | 3/2020 | McNair | |
| 10,622,099 B2 | 4/2020 | Cox et al. | |
| 11,367,519 B1 * | 6/2022 | Heldman | A61M 5/142 |

(Continued)

FOREIGN PATENT DOCUMENTS

| | | |
|---|---|---|
| CN | 105765586 B | 4/2020 |
| GB | 2575740 A | 1/2020 |

(Continued)

OTHER PUBLICATIONS

Lim et al., Forecasting Treatment Responses Over Time Using Recurrent Marginal Structural Networks, 2018, 32nd Conference on Neural Information Processing Systems (Year: 2018).*

(Continued)

*Primary Examiner* — Karen A Hranek
(74) *Attorney, Agent, or Firm* — Erik Swanson; Andrew M. Calderon; Calderon Safran & Cole P.C.

(57) ABSTRACT

A system may receive a query for a patient evaluation. The system may then receive historical patient information or hospital data, current medical information, patient information, and testing information. The system may then use the received information to generate a set of rules using a neural network and uses the rules to process an evaluation for the patient.

20 Claims, 10 Drawing Sheets

(56) References Cited

U.S. PATENT DOCUMENTS

| | | | |
|---|---|---|---|
| 2002/0077756 A1* | 6/2002 | Arouh | G16B 20/00 |
| | | | 435/6.16 |
| 2004/0030503 A1* | 2/2004 | Arouh | G16B 40/20 |
| | | | 702/20 |
| 2005/0216200 A1* | 9/2005 | Urquidi-MacDonald | |
| | | | G16H 20/10 |
| | | | 702/19 |
| 2014/0279746 A1* | 9/2014 | De Bruin | G16H 10/60 |
| | | | 706/46 |
| 2016/0328526 A1* | 11/2016 | Park | G06N 20/20 |
| 2019/0034591 A1* | 1/2019 | Mossin | G06N 3/0445 |
| 2019/0164632 A1* | 5/2019 | Jung | G16C 20/30 |
| 2019/0216452 A1 | 7/2019 | Nawana et al. | |
| 2019/0333636 A1 | 10/2019 | Bennett et al. | |
| 2019/0371450 A1* | 12/2019 | Lou | G16H 20/40 |
| 2020/0098477 A1 | 3/2020 | Peták et al. | |
| 2020/0103394 A1 | 4/2020 | Dennis et al. | |
| 2020/0111576 A1* | 4/2020 | Hart | G16H 10/20 |
| 2020/0118458 A1 | 4/2020 | Shriberg et al. | |
| 2020/0152333 A1* | 5/2020 | Tomasev | G06N 3/0454 |
| 2020/0273578 A1* | 8/2020 | Kutzko | G06N 20/00 |
| 2020/0275885 A1* | 9/2020 | Tang | G06N 5/046 |
| 2020/0356846 A1* | 11/2020 | Saripalli | G06N 3/0445 |
| 2020/0365270 A1* | 11/2020 | Kazemi Oskooei | G16B 20/00 |
| 2020/0380339 A1* | 12/2020 | Branson | G06N 3/0499 |
| 2021/0035672 A1* | 2/2021 | Gobburu | G16H 20/10 |
| 2021/0082575 A1* | 3/2021 | Ji | G06N 3/08 |
| 2021/0142910 A1* | 5/2021 | Hafez | G06F 3/011 |
| 2021/0202102 A1* | 7/2021 | Bostic | G16H 40/20 |
| 2021/0287805 A1* | 9/2021 | Ko | G06N 3/0445 |

FOREIGN PATENT DOCUMENTS

| | | | |
|---|---|---|---|
| WO | 2019022779 A1 | 1/2019 | |
| WO | WO-2019215055 A1 * | 11/2019 | G16H 20/10 |
| WO | 2020021542 A1 | 1/2020 | |
| WO | 2020023865 A1 | 1/2020 | |
| WO | 2020037244 A1 | 2/2020 | |
| WO | WO-2021185936 A1 * | 9/2021 | |

OTHER PUBLICATIONS

Wang et al., Supervised Reinforcement Learning with Recurrent Neural Network for Dynamic Treatment Recommendation, Aug. 2018, KDD 2018 (Year: 2018).*

Norgeot, Deep Learning in Personalized Medicine: Applicaitons in Patient Similarity, Prognosis, and Optimal Treatment Selection, 2019, Dissertation submitted to the Graduate Division of the University of California San Francisco (Year: 2019).*

Mell et al., "The NIST Definition of Cloud Computing," Recommendations of the National Institute of Standards and Technology, U.S. Department of Commerce, Special Publication 800-145, Sep. 2011, 7 pages.

* cited by examiner

ENHANCEMENT OF PATIENT OUTCOME FORECASTING

BACKGROUND

Aspects of the present disclosure relate to drug prescriptions, more particular aspects relate to enhancement of patient outcome forecasting in relation to drug prescriptions.

A prescription drug is a pharmaceutical drug that legally requires a medical prescription to be dispensed. In the United States, the Federal Food, Drug, and Cosmetic Act defines what substances require a prescription for them to be dispensed by a pharmacy. The federal government authorizes physicians (of any specialty), physician assistants, nurse practitioners and other advanced practice nurses, veterinarians, dentists, and optometrists to prescribe any controlled substance. They are then issued unique Drug Enforcement Act numbers; many other mental and physical health technicians, including basic-level registered nurses, medical assistants, emergency medical technicians, most psychologists, and social workers, for example, do not have the authority to prescribe any legend drugs or controlled drugs. Legend drugs are another name for drugs requiring a prescription.

BRIEF SUMMARY

The present disclosure provides a method, computer program product, and system of enhancement of patient outcome forecasting. In some embodiments, the method includes receiving a query for a patient evaluation for a patient, receiving historical information for the patient, receiving current medical information, including a prescription of a medication for the patient, receiving patient data, training a neural network based on the historical information for the patient, generating a set of rules using the neural network, and forecasting, by the neural network with the rules an outcome for the patient based on the current medical information and the patient data.

Some embodiments of the present disclosure can also be illustrated by a computer program product comprising a computer readable storage medium having program instructions embodied therewith, the program instructions executable by a computer to cause the computer to receive a query for a patient evaluation for a patient, receive historical information for the patient, receive current medical information, including a prescription of a medication for the patient, receive patient data, train a neural network based on the historical information for the patient, generate a set of rules using the neural network, and forecast, by the neural network with the rules an outcome for the patient based on the current medical information and the patient data.

Some embodiments of the present disclosure can also be illustrated by a system comprising a processor and a memory in communication with the processor, the memory containing program instructions that, when executed by the processor, are configured to cause the processor to perform a method, the method comprising receiving a query for a patient evaluation for a patient, receiving historical information for the patient, receiving current medical information, including a prescription of a medication for the patient, receiving patient data, training a neural network based on the historical information for the patient, generating a set of rules using the neural network, and forecasting, by the neural network with the rules an outcome for the patient based on the current medical information and the patient data.

DETAILED DESCRIPTION

Aspects of the present disclosure relate to forecasting patient outcomes, and more specifically, to accurately predicting the outcome of a patient taking prescription medication. While the present disclosure is not necessarily limited to such applications, various aspects of the disclosure may be appreciated through a discussion of various examples using this context.

Currently, healthcare industry practitioners including doctors and specialists have no systematic method (or a system driven solution) that looks at historical medicine/drug intake decision data for a patient over a time series and delivers an accurate prediction for the next drug prescription phase based on past drug decision data. Likewise, healthcare industry practitioners, including doctors and specialists, currently have no system and/or solution that looks at the impact of administering multiple drugs to one patient suffering from multiple ailments and getting treatment from different doctors during an overlapping treatment window.

Healthcare industry practitioners, including doctors and specialists, today have no system or solution that looks at historical medicine decision data and forecasts cure-ability of a patient with precision medicine modelling.

In some embodiments, a system, method, and computer program product for precision forecasting of patient disposition for a medicine prescription. In some embodiments, a decision cloud is used to create a decision abstraction analytical interface for doctors considering prescribing a medication to a patient. The decision abstraction analytical interface provides doctors with precision medicine forecasts that analyze a patient's ailment and treatment history. The ailment and treatment history includes administration of medicine and medical tests that were administered in each ailment instance and the decision abstraction analytical interface provides a corelated view of all the decisions that were taken during symptom, diagnosis, prescription, medication & treatment, recovery and outcome phases.

In some embodiments, the doctor uses a health care decision cloud system (HCDCS) to query, using a patient ID (PID), the outcome of the patient taking a medication over a time range. Herein ID stands for some sort of identification. For example, ID could be an ID number, a driver's license number, a name, etc. In some embodiments, the (HCDCS) generates a health care decision cloud time series view showing and inter-related graph of a patient's historical ailments, medicine usage, and testing. Looking at the patient's health care decision cloud analysis the doctor may be shown generated alerts and warnings data with regards to use of a particular drug.

In some embodiments, the system uses a neural network to perform a drug simulation to generate a curability forecast. In some embodiments, the system may also generate alerts for medicine issues.

Figure 1:
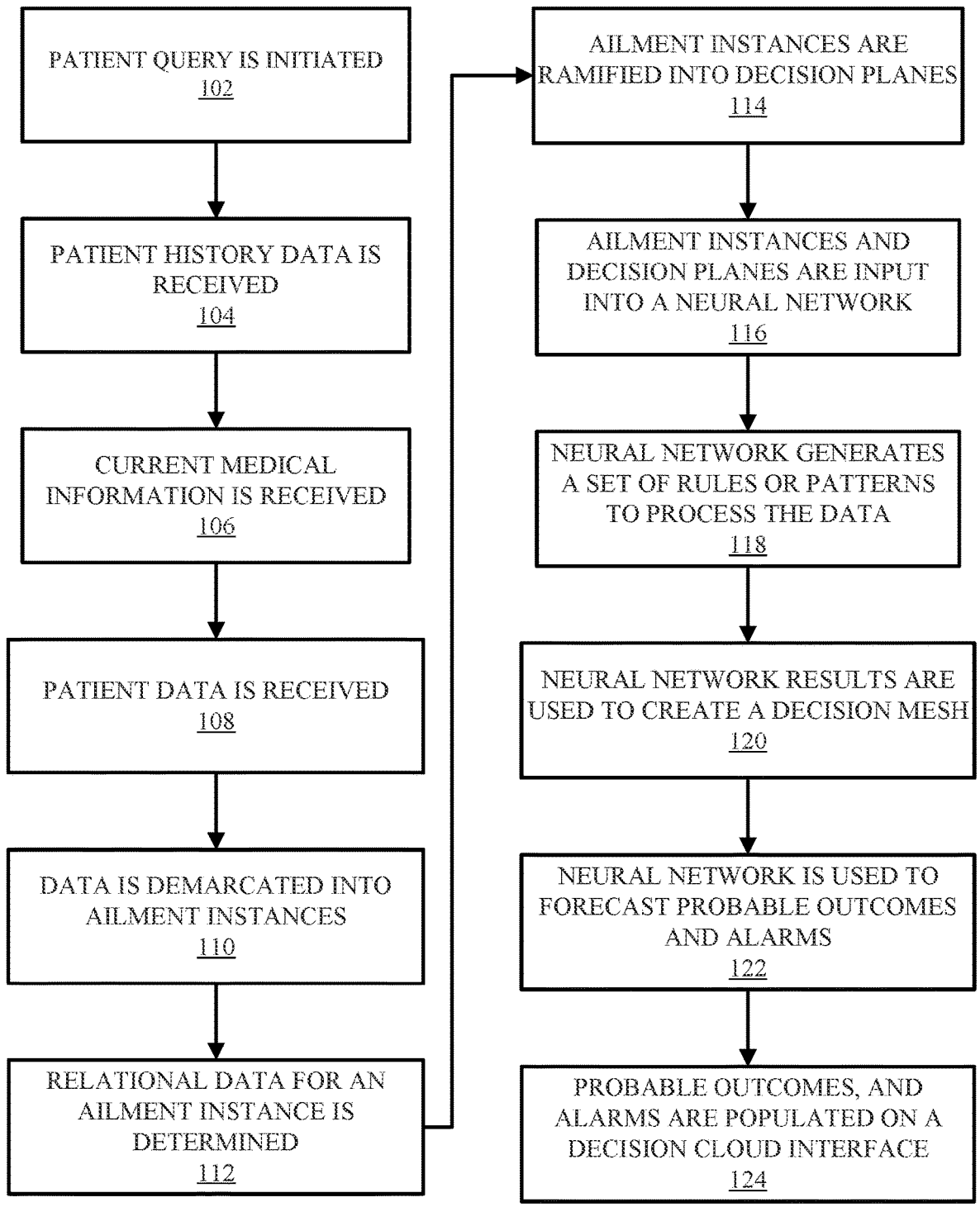
FIG. 1 example method for enhancement of patient outcome forecasting according to various embodiments of the present invention.

FIG. 1 illustrates an example method 100 for precision forecasting of patient disposition for a medicine prescription. Method 100 may be performed, for example, by a computer system controlling one or more neural networks. Method 100 begins with block 102, where a patient query for an evaluation is initiated. In some embodiments, the patient query is initiated by a medical professional using a health care decision cloud system (HCDCS). For example, a doctor may initiate the query during a medical examination visit.

In block 104, patient history data (e.g., historical information for the patient) is received by the HCDCS. In some embodiments, the patient history data includes medical data that may be of record. For example, the patient history data may include prior medical tests, prior symptoms, prior diagnosis, prior medicine prescriptions, prior ailments, prior ailment outcomes (e.g., resolved, not resolved), etc.

In block 106, current medical information (including doctor decision data) is received by the HCDCS. Doctor decision data examples are given in the description of FIG. 2. For example, current medical information may include what tests to perform, results of said tests, one or more medications being prescribed, medical observations and/or a diagnosis for the patient.

In block 108, patient data (including patient decision data) is received. Patient data and/or patient decision data examples are given in the description of FIG. 2. For example, patient data and/or patient decision data may include a decision of a general practitioner or a specialist.

Figure 2:
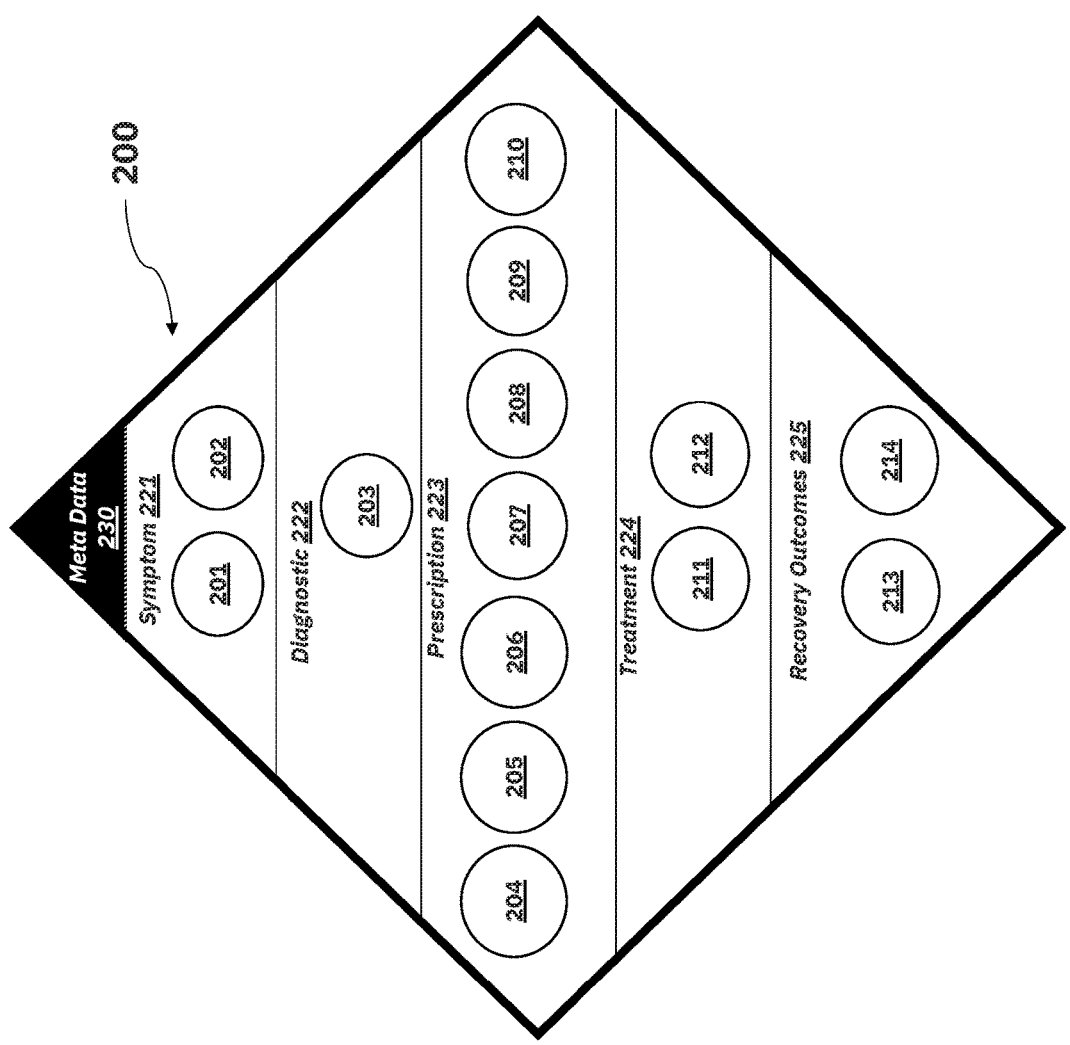
FIG. 2 illustrates an exemplary ailment instance with decision plane data organization according to various embodiments of the present invention.

In block 110, received data is demarcated into ailment instances. An example ailment instance demarcation is shown in FIG. 2. An ailment instance (AINS) may consist of meta data and decision plane data pertaining to a particular ailment across different stages of the recovery process. In some embodiments, the demarcation may be performed on a current ailment instance, and previous ailment instances derived from the historical data gathered in 104.

Figure 3:
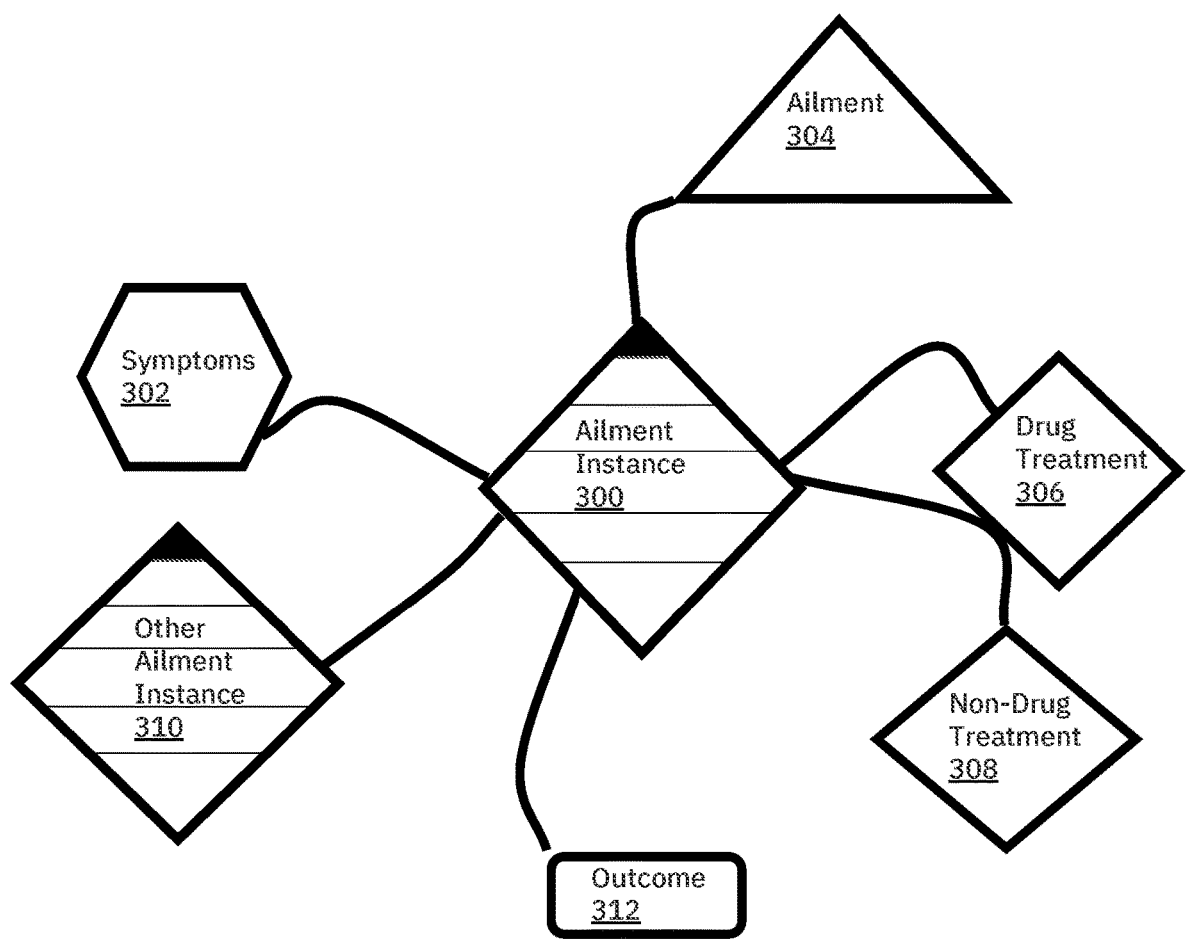
FIG. 3 illustrates an exemplary ailment instance context diagram according to various embodiments of the present invention.

In block 112, relational data for an ailment instance is determined. An example ailment instance with relational data is depicted in FIG. 3. In some embodiments, an ailment instance consists of meta data 230 and decision plane data pertaining to a particular ailment across different stages of the recovery process. In some embodiments, data gathered in blocks 106 and 108 is populated into relational data categories for the current instance. In some embodiments, data gathered in block 104 is populated into previous ailment instances. See FIG. 3 for examples of populating data into relational data categories. In some embodiments, the relational data may be determined for the current ailment instance and previous ailment instances derived from the historical data gathered in 104.

Figure 4:
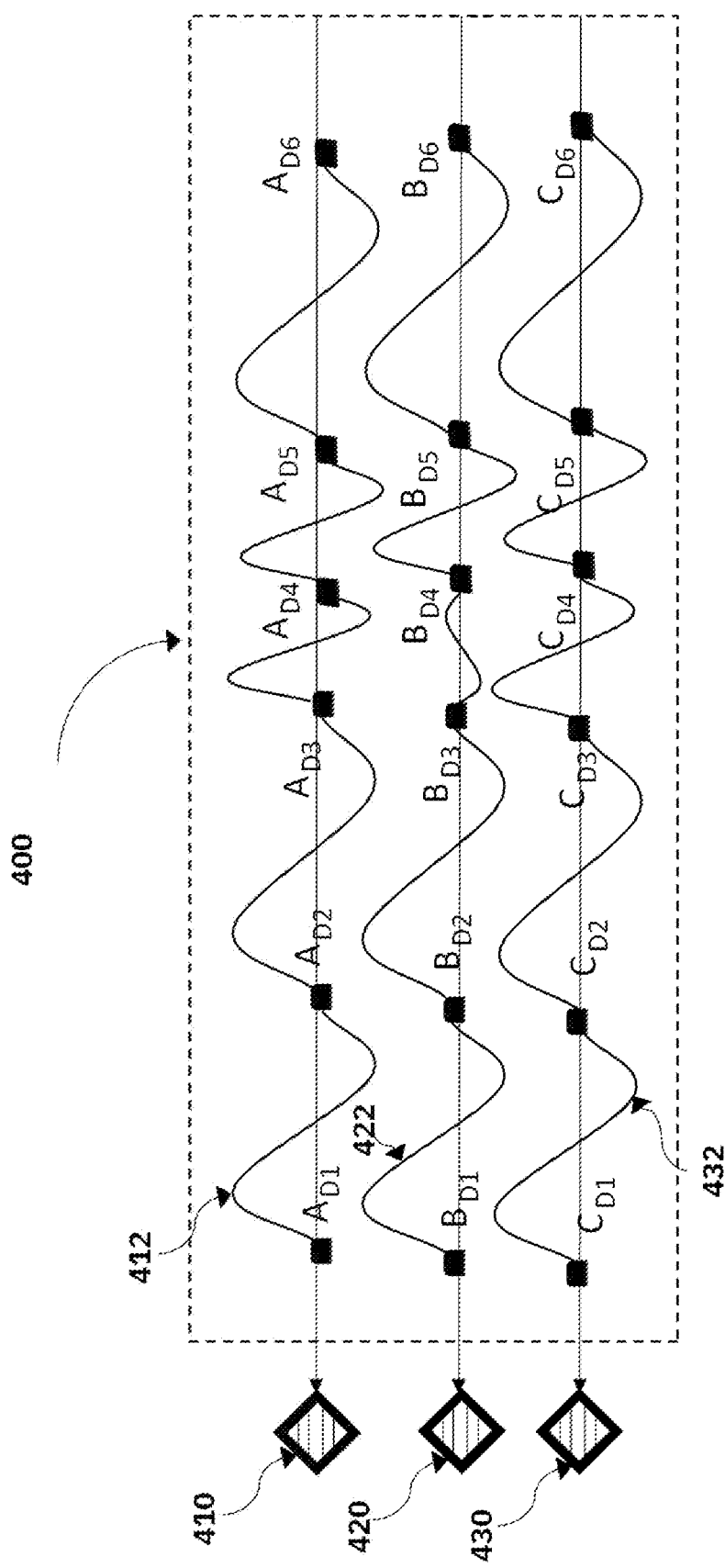
FIG. 4 illustrates an exemplary decision plane with a CDN according to various embodiments of the present invention.

In block 114, the ailment instances are ramified into decision planes. An example decision plane is depicted in FIG. 4. In some embodiments, decision planes are used to corelate decision plane data for two or more ailment instances to identify relations between ailment instances. For example, two or more ailment instances with similar symptoms may have a similar outcome when the same medicine is used. In some embodiments, the current ailment instance may be ramified into a decision plane, and previous ailment instances may be ramified into decision planes.

Figure 7:
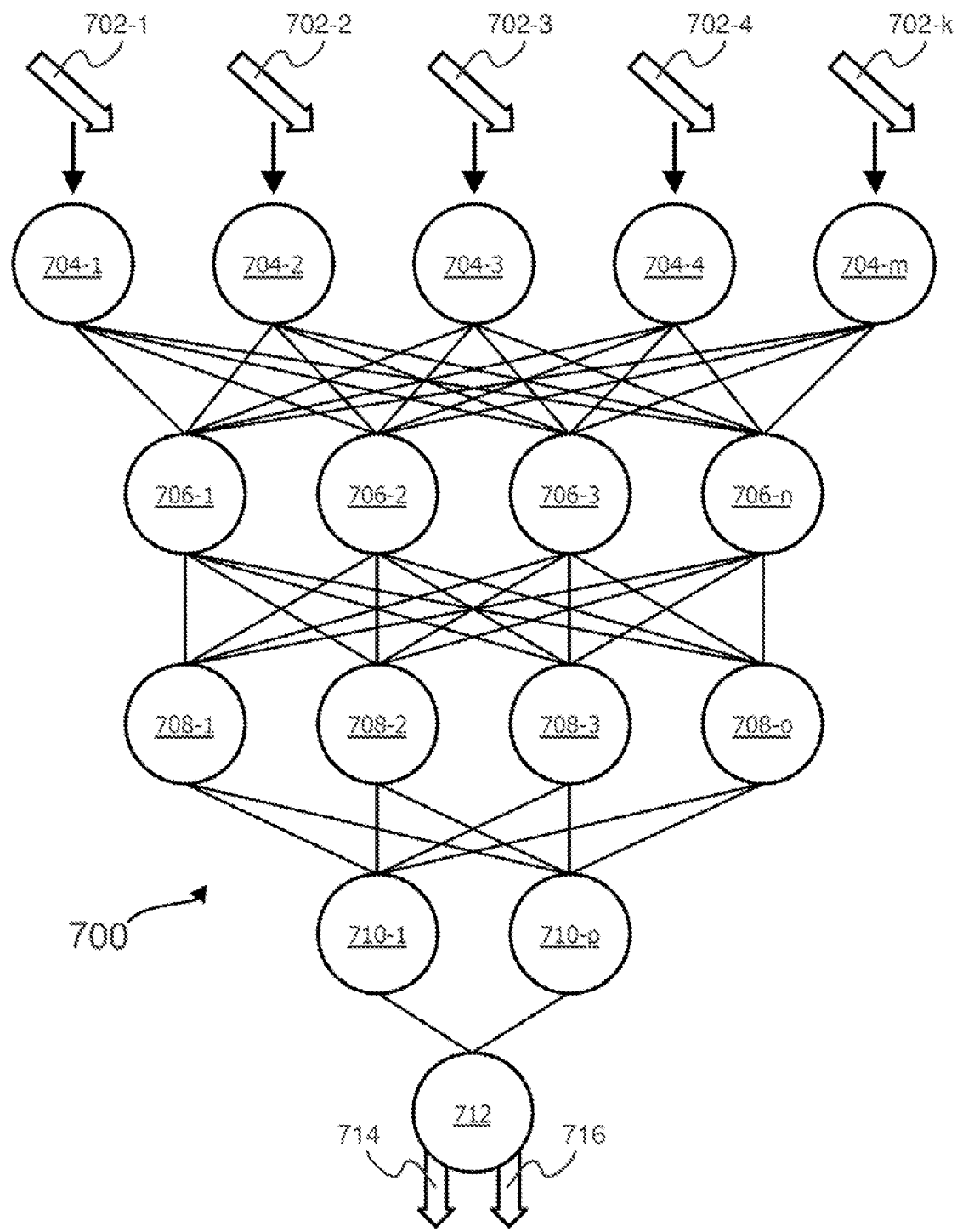
FIG. 7 illustrates the representative major components of a neural network that may be used in accordance with embodiments.

In block 116, the ailment instances (both historical and current) and decision planes are input into a neural network. In some embodiments, a neural network may process and analyze input data (e.g., data gathered in blocks 106 and 108), by recognizing patterns in the input data and comparing those patterns to patterns related to historical ailment instances (e.g., data gathered in block 104) on which the neural network has been trained. In some instances, the patterns may be referred to as rules herein. In some embodiments, the neural network may be trained with historical ailment instances as depicted in FIG. 7 and discussed below.

In block 118, the neural network generates a set of rules or patterns to process the data. In some embodiments, ramifying the ailment instances into decision planes creates a relational network that provides the neural network with a basic framework for forming the patterns that are created in the training of the network. This basic framework makes the training of the neural network consume fewer resources and makes neural network prediction more accurate.

Table 1 below lists some example rules that a health care decision cloud system (HCDCS) may generate using a neural network. In some embodiments, the HCDCS may train the neural network to generate results pertaining to specific policies and sub-policies. Table 1 demonstrates a selection of example policies and sub-policies along with example rules that the neural network may generate for those policies.

TABLE 1

Rules for specific policies and sub-policies.

| Policy | Sub-Policy | Sub-Policy Description | Policy Rule Criteria/Formulae |
|---|---|---|---|
| Drug Co-relation & Warnings | Drug Overdosage | Patient consuming same drug from multiple prescriptions due to multiple Ailments | If Count(AID_Status = active) > 1, Then Check for match on Drug Name column in Table04 of Active AID(s) then generate an Overdosage alert or If AID(s) in last 30 days have a matching Drug name in Table04 Column Drug Name |

TABLE 1-continued

Rules for specific policies and sub-policies.

| Policy | Sub-Policy | Sub-Policy Description | Policy Rule Criteria/Formulae |
|---|---|---|---|
| | Excess Medicine Intake | Medicine Intake in a patient is way too high and can impact overall health condition. | then generate an Overdosage alert For X = 1, n where X = Drug name and 1..n is sequence of prescribed drugs then {If Drug dosage from any drug X in Table04 is greater than Patient Weight * Permissible Max Dosage for that drug as per FDA in mg/kg then return Alert "Excess Dosage of" + "X"} |
| | Potential chronic Impact to an Organ | Excess use of a particular type of medicine for specialized treatment in combination with other drugs. | If System generates a Drug Overdosage alert, read the AID_Label, from the AID Label database query the potentially impacted Organ and set an alert. |
| | Immunity Alert | Not Cured or Partially cured with a series of similar and related Ailments where same drug is used | List Common Drug from Table04 of ALL AID(s) with Related Ailments with at least 2 Predecessors |
| Medicinal Success Rate | Overall Medicinal Success Rate | % relating to how many times the patient was cured fully without any re-occurance of the ailment. | (Count(Isolated Ailments)/Count(All Ailments) * 100 |
| Cure-ability Forecast | Drug vs Cure Ratio | Ability to calculate in % use of a particular drug leading to cure based on historical intake of the same drug by this patient. | Curability(PID, X) = (Count(All Ailments where {this} Drug was used on this patient historically where Outcome was Cured)/Count(All Ailments)) * 100. Where PID is patient ID and X is the drug name |

Figure 5:
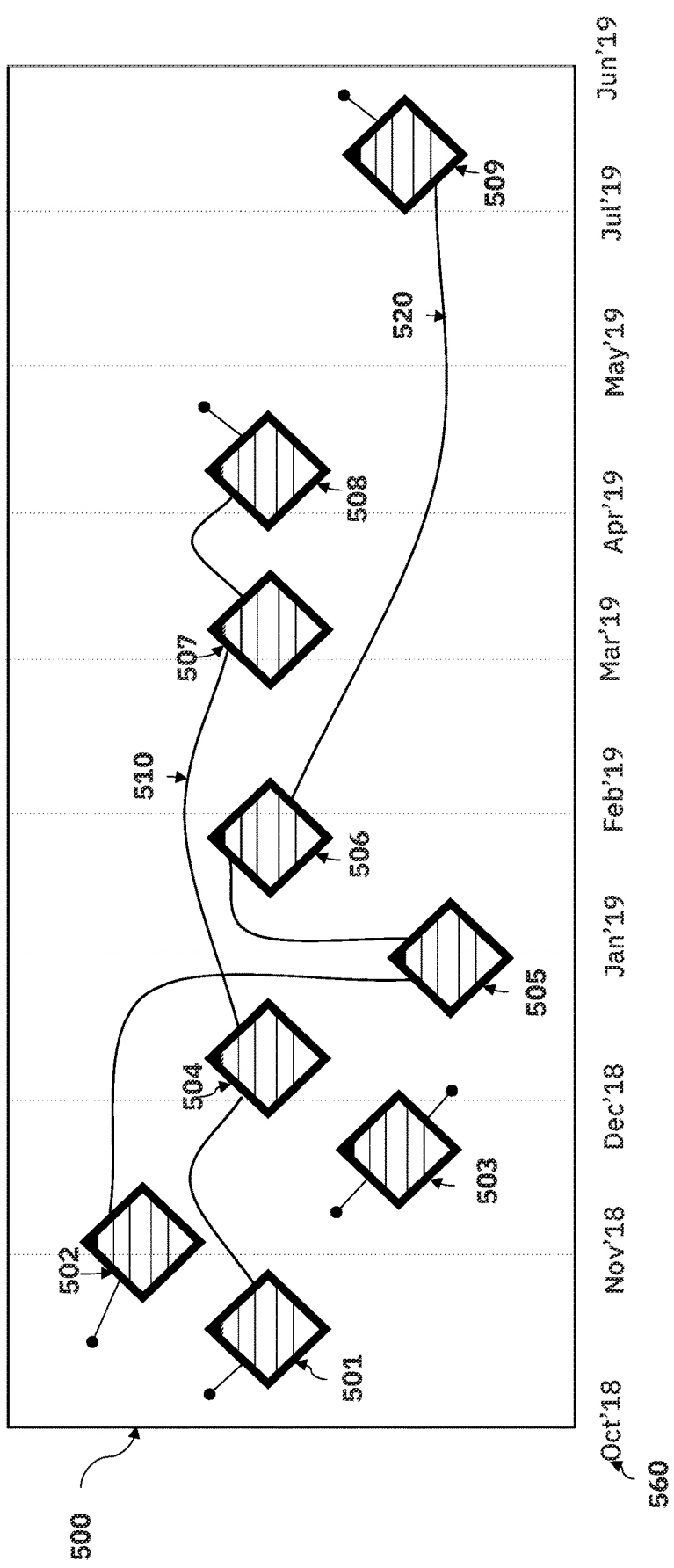
FIG. 5 illustrates exemplary decision mesh according to various embodiments of the present invention.

In block 120, the neural network results are used to create a decision mesh. In some embodiments, a decision mesh depicts multiple ailment instances to trace lineage to origin of the ailment and provides a discovery mechanism that enables study of all related ailments found over a time-range. An exemplary decision mesh is depicted in FIG. 5 and discussed below. The relationship between multiple ailments is derived by running the neural network over the discovered ailment instances. For example, the neural network may determine that another drug the patient is taking is in the drug the current doctor is prescribing.

In block 122, the neural network is used to forecast probable outcomes and/or medicine alarms. In some embodiments, probable outcomes may include likelihood that symptoms are reduced, a resolution of an underlying condition, and/or a curing of an ailment or condition. In some embodiments, the outcomes may be similar to the policies and sub-policies listed in table 1. For example, a drug co-relation impact may be that the current drug the doctor is prescribing is likely to have a bad reaction with another drug the patient is prescribed from another doctor, and organ damage may result. In another example, an alarm may be a percentage chance that a drug or treatment resolves the patients symptoms, cures the patient of the ailment, and/or a percentage chance that a patient would be cured fully without any re-occurrence of the ailment.

Figure 6:
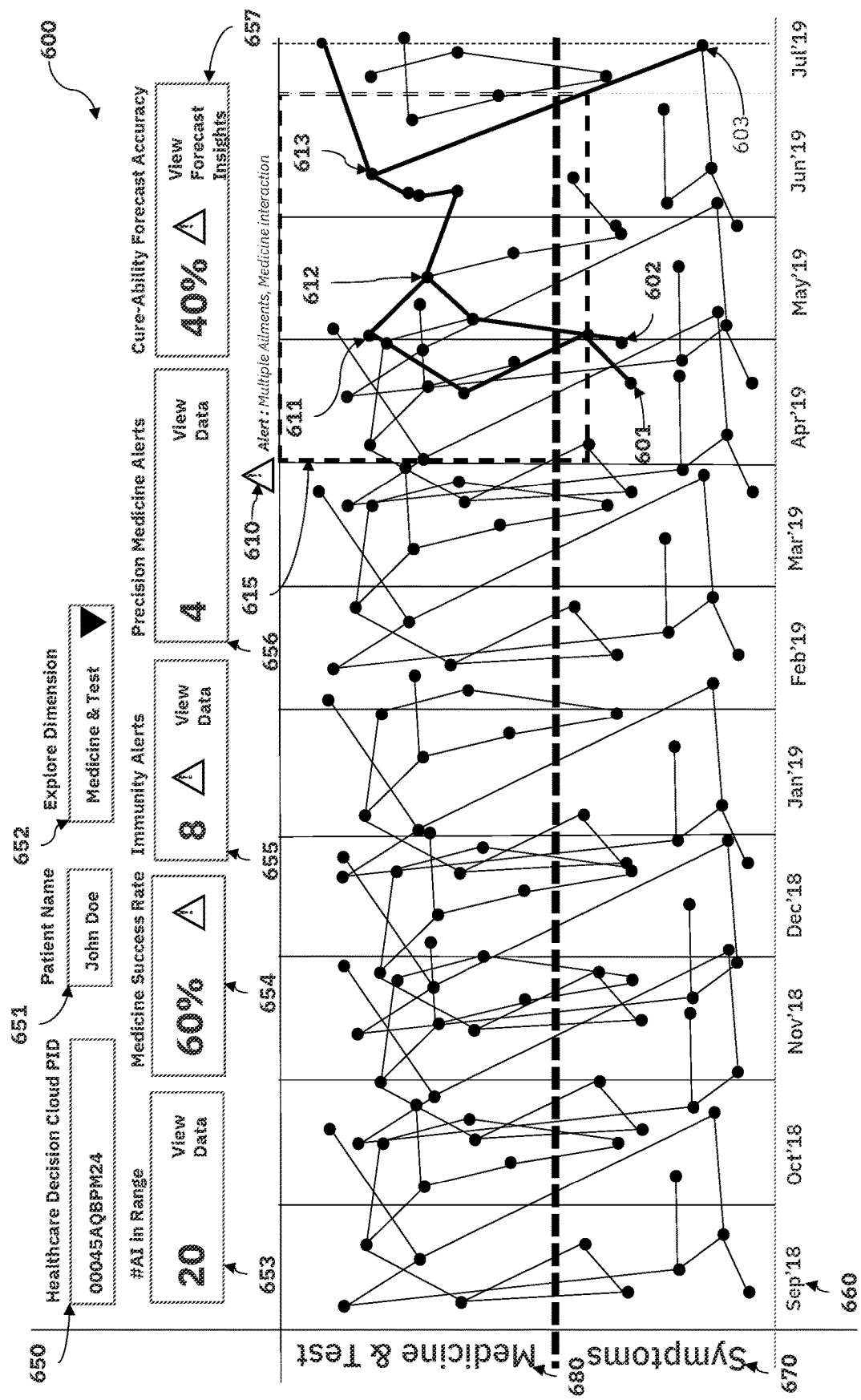
FIG. 6 illustrates an exemplary healthcare decision cloud interface according to various embodiments of the present invention.

In block 124, the ailment instances, probable outcomes, and alarms are populated on a decision cloud interface. An exemplary decision cloud interface is depicted in FIG. 6.

Exemplary ailment instance 200 is shown in FIG. 2 with decision plane data organization. In some embodiments, an ailment instance consists of meta data 230 (represented by the triangle at the top of ailment instance 200) and decision plane data pertaining to a particular ailment across different stages of the recovery process. Examples of ailment instance meta-data may include, patient identification number (PID), ailment instance identifier (AID), origin/reported date, ailment description, ailment symptoms, doctor's ID (DID), and/or clinic/hospital ID (CHID). In some embodiments, decision plane data 201-214 may be data received regarding the ailment instance (e.g., a doctors visit) on which the system may focus a comparison in a decision plane (See FIG. 4 for details on decision planes). For example, depicted are some exemplary focus areas with example data points, details follow:

focus area Symptom 221 may include,
    data point 201: decision on general practitioner or specialist and
    data point 202: decision on doctor selection (e.g., which specialist from the option of specialists).
focus area Diagnosis 222 may include,
    data point 203: decision on what tests to perform
focus area Prescriptions 223 may include,
    data point 204: decision on what drug families apply
    data point 205: decision on what drug names to use
    data point 206: decision on drug dosage of each drug in mg
    data point 207: decision on drug frequency for each drug
    data point 208: decision on drug usage duration for each drug
    data point 209: decision on what non-drug treatment to give
    data point 210: decision on any special instructions for non-drug treatment
focus area Treatment 224 may include,
    data point 211: decision to use each of the prescribed drug(s)
    data point 212: decision to fully complete each of the prescribed drug(s)

focus area Recovery outcomes 225 may include,
  data point 213: decision to confirm cure (fully cured, partly cured or not cured)
  data point 214: decision to revisit the doctor if partly/not cured.

Other data points and focus areas are possible. In some embodiments, the data points are routed to a focus area based on when the data point is collected, based on human input, and/or based on a keyword search. For example, symptoms 221 may be before a doctor appointment, diagnosis may be during the doctor appointment, prescription may be at the end of the doctor appointment, and treatment may be after an appointment. In some embodiments, the data points are preconceived questions that are automatically routed to a focus area. For example, for every doctor appointment, the system may ask a doctor to decide if tests are to be performed.

Exemplary ailment instance context diagram is shown in FIG. 3 along with relational data for the ailment instance. In some embodiments, an ailment instance 300 is a point of contact with a medical professional for a specific condition. For example, an ailment instance may be a record of a medical condition, injury, etc. In some embodiments, ailment instances are linked (e.g., ailment instance 300 and other ailment instance 310). For example, an ailment instance may be a doctor visit for the reoccurrence of a chronic condition. More details are provided in FIG. 4 below. In some embodiments, ailment instances are standalone instances that are not directly related to any other ailment instance. For example, an ailment instance may be a nurse visit for an acute injury.

In some embodiments, exemplary ailment instance 300 is connected to one or more relational data points, herein referred to as ailment attributes 302-312, leading to or resulting from the ailment instance. The system uses the ailment attributes 302-312 to derive relationships among multiple ailments, such as other ailment instance 310. Some ailment attributes may lead to an ailment instance. For example, ailment attributes that may lead a patient to go see a doctor may be symptoms 302 and other ailment instances 310 (e.g., a follow up visit). In some embodiments, symptoms are one or more physical or mental characteristics that the patient or medical professional think are abnormal. In some embodiments, other ailment instance 310 may be an ailment instance with one or more ailment attributes that are similar. For example, matching symptoms may be a similarity that links ailment instance 300. In some embodiments, other ailments are future or previous ailments relating to any of the decision plane data (see FIG. 4 for more details) or ailment attributes of the current ailment.

In some embodiments, some ailment attributes are resultant of the decision. Examples of such resultant ailment attributes may be outcomes 312, drug treatment 306, ailment 304, other ailment instances 310, and non-drug treatment 308. For example, drug treatment 306 may be used to treat symptoms 302, to give time for non-drug treatment 306 to solve ailment 304 (e.g., the injury), resulting in a positive outcome 312.

An exemplary decision plane 400 is shown in FIG. 4 with three example ailment instances: ailment instance A 410, ailment instance B 420, and ailment instance C 430. Each of the example ailment instances had several data points D1-D6. These may be similar to data points 201-214 in FIG. 2. In some embodiments, decision plane 400 is used to align one or more data points for one or more ailment instances. For example, AD1, BD1, and CD1 may all be a decision on if the patient is going to see a general practitioner or a specialist (similar to 201 in FIG. 2). In some embodiments, data is correlated on the decision plane by matching the data points in the focus areas between the ailment instances. By correlating the data points before they are fed into the neural network, it may make rule generation faster and the machine learning algorithms more focused. In an example, AD3 is a decision to use a first family of drugs, BD3 is a decision to use a second family of drugs, and CD3 is the decision to use the first family of drugs again. Thus, ailment instance A 410 may be correlated closely with ailment instance C 430, and not ailment instance B 420. In some embodiments, the lines 412, 422, and 432 connected to the ailment instances 410, 420, and 430 are vector representations of the decisions, allowing correlation by a degree of matching the lines. Following the previous example, line 422 does not match line 412 after D3, but line 432 does match line 412 after D3. The resulting improvement to the system processing may increase the speed at which a computer system may process a likelihood of a drug treatment being a success or process any drug alerts.

FIG. 5 depicts an exemplary decision mesh 500. In some embodiments, exemplary decision mesh 500 provides the capability to co-relate multiple ailment instances, to trace lineage to an origin of the ailment, and to provide a discovery mechanism that enables study of all related ailments found over a time-range. Exemplary decision mesh 500 depicts the ailment instances 501-509 for a patient over a given time period, shown by axis 560. In some embodiments, a line, such as line 510 or 520 connects one or more ailment instances that are related. For example, line 520 links ailment instances 502, 505, 506, and 509. For example, ailment instance 502 may be a patient being seen for a head ache, ailment instance 505 may be a patient later being prescribed a medication for a migraine, ailment instance 506 may be a patient getting an test done on their brain, and ailment instance 509 may be a diagnosis of an abnormal growth in the brain. For example, ailment instances 501, 504, 507, and 508 may all be related to a compound leg fracture. For example, instance 503 may be related to a sprained finger that was resolved with a pain reliever/inflammation reducer and never flared up again. In some embodiments, the lines and instances may be color coded. For example, line 520 and ailment instances 502, 505, and 506, may be red since they are linked to current ailment instance 509. In some embodiments, some ailment instances may be standalone instances that do not link to other instances. For example, ailment instance 503 does not link to any other ailment instance. In some embodiments, ailment instances may be determined to be linked with a decision plane, see FIG. 4. For example, ailment instances 502, 505, 506, and 509 may all have a common symptom.

FIG. 6 depicts an exemplary healthcare decision cloud interface (HDCI) 600. In some embodiments, HDCI 600 provides a way to trace prescriptions and tests that the patient has received. In some embodiments, populating all data on a single view provides easy access for a medical professional and uses less system resources that it takes to get similar information from several different applications and views. In some embodiments, HDCI provides basic information such as the healthcare decision cloud patient ID (PID) 650, the patient name 651, and the particular view shown (with explore dimension 652). For example, the medicine and test graph 680 is being shown. In some embodiments, the HDCI depicts more detailed information such as ailment instances in range 653, predicted medicine success rate 654 for a particular medicine, immunity alerts for the particular medicine 655, precision medicine alerts 656 for the particular medicine, and overall cure-ability forecast accuracy 657 for a particular ailment. In some embodiments, specific decision plane data (see FIG. 2) is plotted with linking lines for related decision plane data. For example, data points medicine 611, medicine 612, test 613, symptom 601, symptom 602, and symptom 603 are all linked since symptoms 601, 602, and 603 may all be from the same ailment and medicine 611, medicine 612, and test 613 may have all been treatments or testing derived from those symptoms. In this example, symptom 601 may be a cough, symptom 602 may be a sore throat, and symptom 603 may be a fever while 611 may be cold medicine, 612 may be some cough drops, and 613 may be a throat culture. In some embodiments, the datapoints may be populated with reference to a timeline. For example, timeline 660 shows when the medicines were prescribed or the symptoms reported. In some embodiments, the datapoints that are in the range for the alert may be outlined. For example, box 615 outlines the data points in the range for alert 610. In some embodiments, the graph may be segmented to differentiate types of decision plane data. For example, HDCI 600 shows medicine & test section 680, and symptoms section 670.

As has been discussed previously, a neural network may process and analyze input data (here, a combination of historical patient data, doctor decisions, and patient decisions) by recognizing patterns in the input data and comparing those patterns to patterns (e.g., rules) related to historical patient data on which the neural network has been trained. For example, a neural network may recognize several patterns in the data expressed by an input vector for a particular patient data. The neural network may then associate some of those patterns with the patterns associated with historical patient data that the neural network has been trained (e.g., by human-supervised training or automatic training) to predict a patient outcome or a medicine alert.

In some embodiments, data input into a neural network may take the form of a vector. A vector may be a one-dimension matrix (e.g., a matrix with one row and many columns) of numbers, each of which expresses data related to, for example, symptoms, diagnosis, prescriptions, treatments or recovery outcomes. A vector may also be referred to herein as an "input vector," a "feature vector," or a "multi-dimension vector." For example, as previously discussed, this vector may include doctor selection, what tests are performed, what drugs are prescribed, what drug dosage is used, was the drug taken to completion, and was the patient cured, among others.

Such a neural network is illustrated in FIG. 7. In FIG. 7, neural network 700 may be trained to predict patient outcomes based on information or decisions gathered regarding patients (e.g., in blocks 104, 106, and 108). The inputs of neural network 700 are represented by feature vectors 702-1 through 702-$k$. These feature vectors may contain all information that is available after the data is ramified into decision planes, and, in some embodiments, relational data for one or more ailments. In some embodiments, feature vectors 702-1 through 702-$k$ may be identical copies of each other. In some embodiments, more instances of feature vectors 702 may be utilized. The number of feature vectors 702-1 through 702-$k$ may correspond to the number of neurons in feature layer 704. In other words, in some embodiments, the number of inputs 702-1 through 702-$k$ (i.e., the number represented by m) may equal (and thus be determined by) the number of first-layer neurons in the network. In other embodiments, neural network 700 may incorporate 1 or more bias neurons in the first layer, in which case the number of inputs 702-1 through 702-$k$ may equal the number of first-layer neurons in the network minus the number of first-layer bias neurons.

Feature layer 704 contains neurons 701-1 through 701-$m$. Neurons 704-1 through 704-$m$ accept as inputs feature vectors 702-1 through 702-$k$ and process the information therein. Once vectors 702-1 through 702-$k$ are processed, neurons 704-1 through 704-$m$ provide the resulting values to the neurons in hidden layer 706. These neurons, 706-1 through 706-$n$, further process the information, and pass the resulting values to the neurons in hidden layer 708. Similarly, neurons 708-1 through 708-$o$ further process the information and pass it to neurons 710-1 through 710-$p$s. Neurons 710-1 thorough 710-$p$ process the data and deliver it to the output layer of the neural network, which, as illustrated, contains neuron 712. Neuron 712 may be trained to calculate two values—value 714 and value 716. Value 714 may represent the likelihood that a patient is likely to have a positive outcome after taking a drug. Value 716, on the other hand, may represent one or more drug alerts.

In some embodiments, neural network 700 may have more than 5 layers of neurons (as presented) or fewer than 5 layers. These 5 layers may each comprise the same amount of neurons as any other layer, more neurons than any other layer, fewer neurons than any other layer, or more neurons than some layers and fewer neurons than other layers. Finally, in some embodiments, the output of output layer 712 may be used to determine the outcome of a patient taking a drug or if there are any alerts for the drug.

Figure 8:
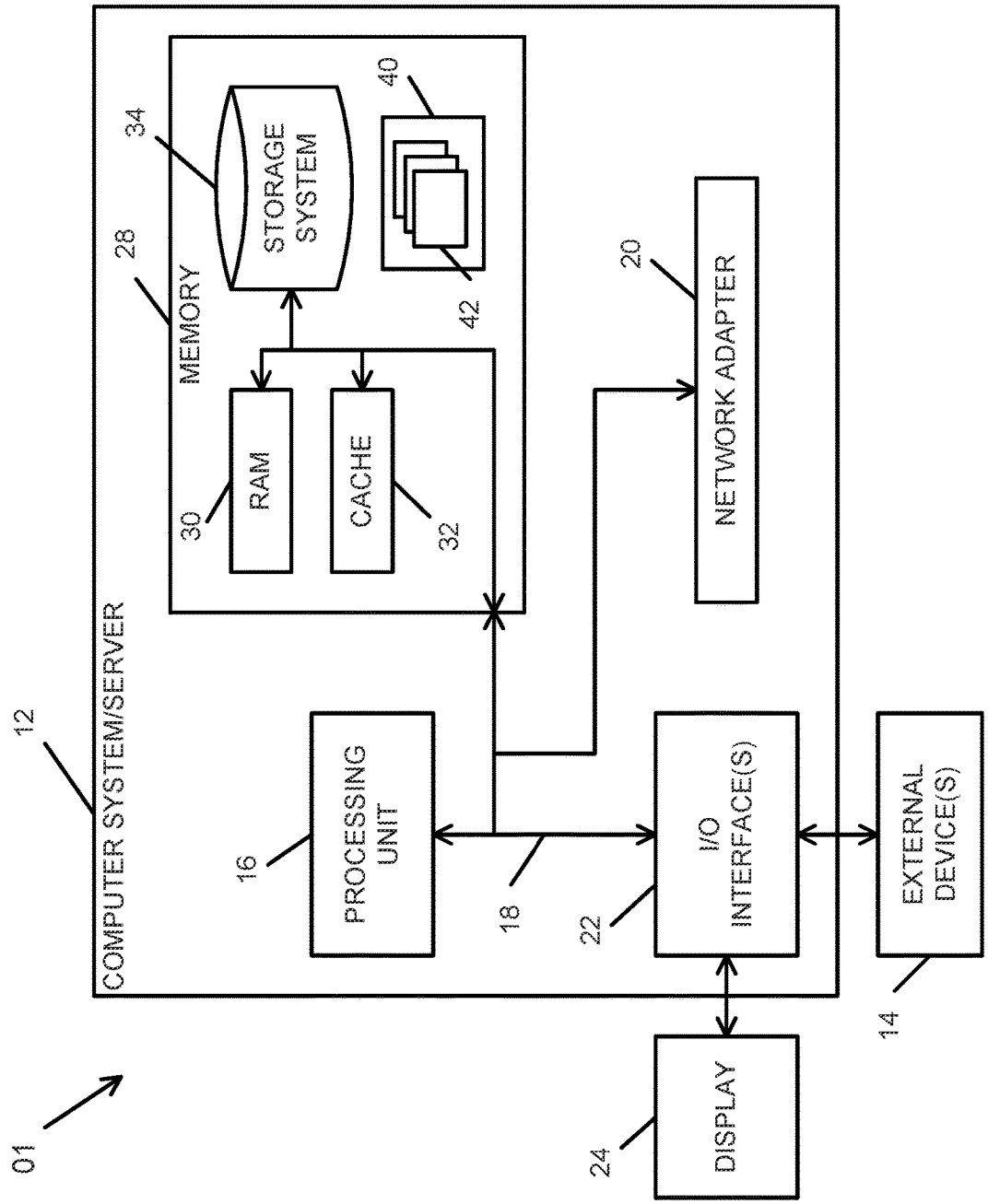
FIG. 8 depicts a computer system according to various embodiments of the present invention.

In an exemplary embodiment, the computer system is a computer system 01 as shown in FIG. 8. Computer system 01 is only one example of a computer system and is not intended to suggest any limitation as to the scope of use or functionality of embodiments of the present invention. Regardless, computer system 01 is capable of being implemented to perform and/or performing any of the functionality/operations of the present invention.

Computer system 01 includes a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices.

Computer system/server 12 may be described in the general context of computer system-executable instructions, such as program modules, being executed by a computer system. Generally, program modules may include routines, programs, objects, components, logic, and/or data structures that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computer system 01 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As is further depicted and described below, memory 28 may include at least one program product having a set (e.g., at least one) of program modules that are configured to carry out the functions/operations of embodiments of the invention.

Program/utility 40, having a set (at least one) of program modules 42, may be stored in memory 28 by way of example, and not limitation. Exemplary program modules 42 may include an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the present invention.

Computer system/server 12 may also communicate with one or more external devices 14 such as a keyboard, a pointing device, a display 24, one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems.

Cloud Computing

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
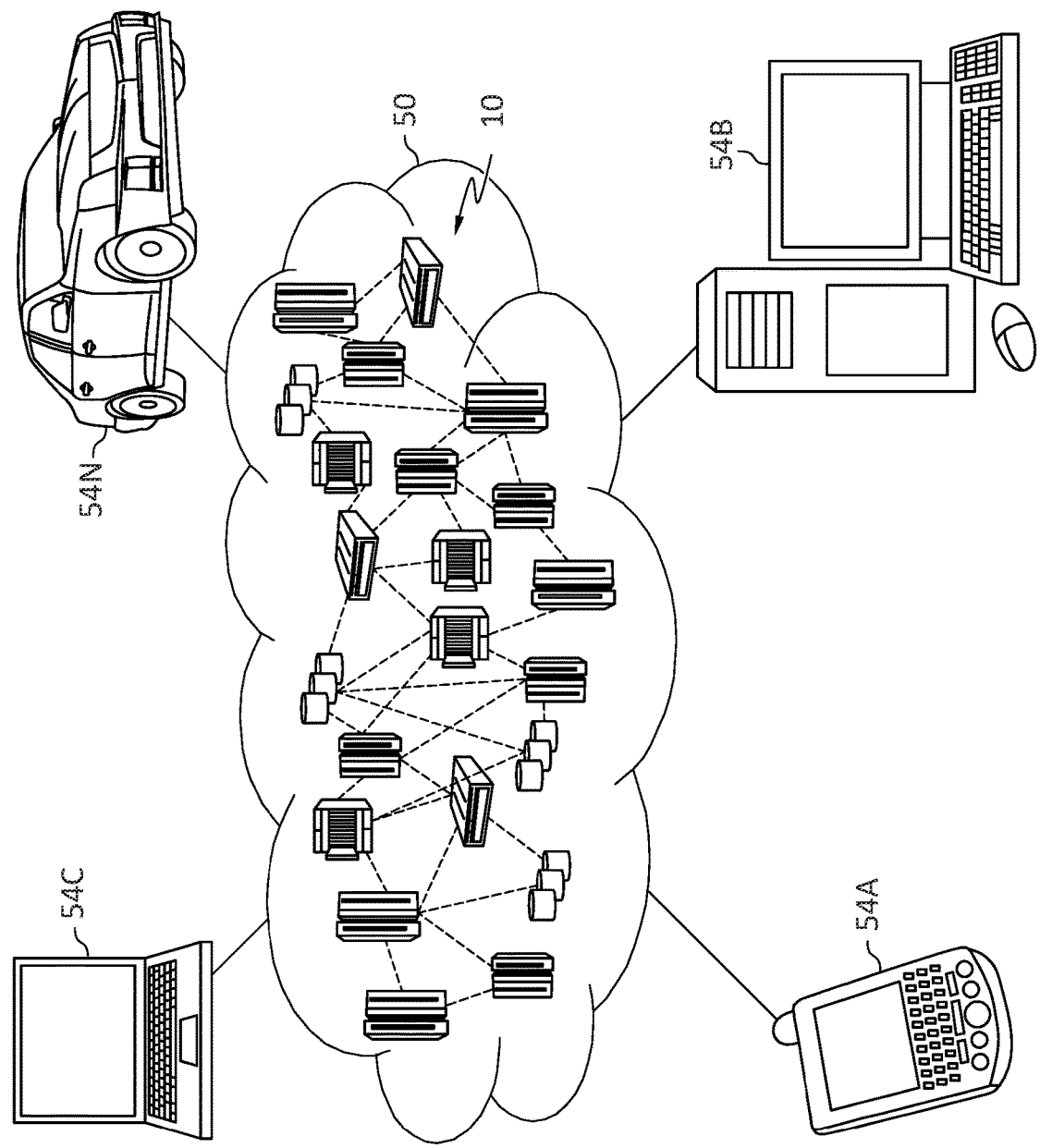
FIG. 9 depicts a cloud computing environment according to various embodiments of the present invention.

Referring now to FIG. 9, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 9 are intended to be illustrative only and that computing nodes 10 and cloud computing environment 50 can communicate with any type of computerized device over any type of network and/or network addressable connection (e.g., using a web browser).

Figure 10:
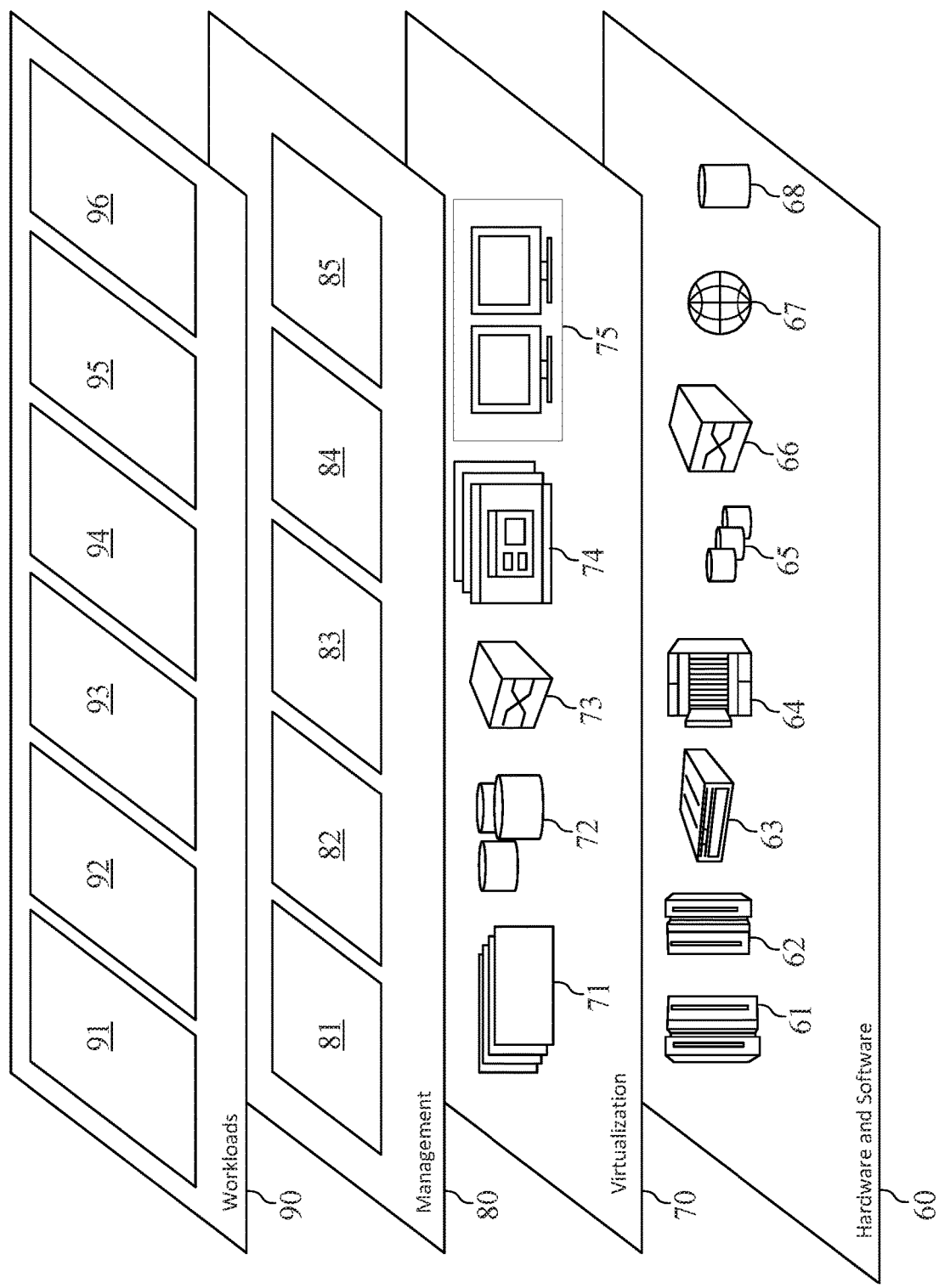
FIG. 10 depicts abstraction model layers according to various embodiments of the present invention.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and predictive neural networks 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method comprising:
   receiving, by at least one processor, a query for a patient evaluation for a patient;
   receiving, by the at least one processor, historical information for the patient, including prior medication used by the patient;
   receiving, by the at least one processor, current medical information, including a prescription of a medication for the patient;
   receiving, by the at least one processor, patient data;
   training a neural network based on the historical information for the patient;
   generating a set of medicine-related rules using the neural network, the set of medicine-related rules comprising patient-specific medication co-relations and warnings, a medication success rate for the patient based on the patient's prior use of the medication of the prescription, and a cure-ability forecast for the medication leading to a patient cure based on historical intake of the same medication of the prescription by the patient; and forecasting, by the neural network with the medicine-related rules, medication effectiveness for the patient taking the medication based on the current medical information and the patient data.

2. The method of claim 1 further comprising:
demarcating the historical information into ailment instances of one or more patient ailments, the ailment instances each comprising metadata and decision plane data pertaining to a particular ailment across different stages of recovery from the ailment, and
determining relational data for the ailment instances based on similarities between the ailment instances.

3. The method of claim 2 further comprising:
ramifying ailment instances into decision planes; and
correlating decision plane data for two or more ailment instances.

4. The method of claim 3 wherein the training is further based on the demarcating, the determining, the ramifying, and the correlating.

5. The method of claim 1, wherein the forecasting further includes:
creating a decision mesh with results from the neural network.

6. The method of claim 1, further comprising:
displaying the outcome on a decision cloud interface.

7. The method of claim 1, wherein the outcome is an impact of the patient taking the medication.

8. The method of claim 7, wherein the outcome is a medication alert for the medication.

9. A computer program product, the computer program product comprising a computer readable storage medium having program instructions embodied therewith, the program instructions executable by a computer to cause the computer to:
receive a query for a patient evaluation for a patient;
receive historical information for the patient, including prior medication used by the patient;
receive current medical information, including a prescription of a medication for the patient;
receive patient data;
train a neural network based on the historical information for the patient;
generate a set of medicine-related rules using the neural network, the set of medicine-related rules comprising patient-specific medication co-relations and warnings, a medication success rate for the patient based on the patient's prior use of the medication of the prescription, and a cure-ability forecast for the medication leading to a patient cure based on historical intake of the same medication of the prescription by the patient; and
forecast, by the neural network with the medicine-related rules, medication effectiveness for the patient taking the medication based on the current medical information and the patient data.

10. The computer program product of claim 9, wherein the program instructions further cause the computer to:
demarcate the historical information into ailment instances of one or more patient ailments, the ailment instances each comprising metadata and decision plane data pertaining to a particular ailment across different stages of recovery from the ailment, and
determine relational data for the ailment instances based on similarities between the ailment instances.

11. The computer program product of claim 10, wherein the program instructions further cause the computer to:
ramify ailment instances into decision planes; and
correlate decision plane data for two or more ailment instances.

12. The computer program product of claim 11 wherein the training is further based on the demarcating, the determining, the ramifying, and the correlating.

13. The computer program product of claim 9, wherein the forecasting further includes:
create a decision mesh with results from the neural network.

14. The computer program product of claim 9, wherein the program instructions further cause the computer to:
display the outcome on a decision cloud interface.

15. A system comprising:
a processor; and
a memory in communication with the processor, the memory containing program instructions that, when executed by the processor, are configured to cause the processor to perform a method, the method comprising:
receiving a query for a patient evaluation for a patient;
receiving historical information for the patient, including prior medication used by the patient;
receiving current medical information, including a prescription of a medication for the patient;
receiving patient data;
training a neural network based on the historical information for the patient;
generating a set of medicine-related rules using the neural network, the set of medicine-related rules comprising patient-specific medication co-relations and warnings, a medication success rate for the patient based on the patient's prior use of the medication of the prescription, and a cure-ability forecast for the medication leading to a patient cure based on historical intake of the same medication of the prescription by the patient; and
forecasting, by the neural network with the medicine-related rules, medication effectiveness for the patient taking the medication based on the current medical information and the patient data.

16. The system of claim 15, wherein the method further includes:
demarcating the historical information into ailment instances of one or more patient ailments, the ailment instances each comprising metadata and decision plane data pertaining to a particular ailment across different stages of recovery from the ailment, and
determining relational data for the ailment instances based on similarities between the ailment instances.

17. The system of claim 16, wherein the method further includes:
ramifying ailment instances into decision planes; and
correlating decision plane data for two or more ailment instances.

18. The system of claim 17 wherein the training is further based on the demarcating, the determining, the ramifying, and the correlating.

19. The system of claim 15, wherein the forecasting further includes:
creating a decision mesh with results from the neural network.

20. The system of claim 15, wherein the method further includes:
displaying the outcome on a decision cloud interface.

* * * * *